Figure 1:
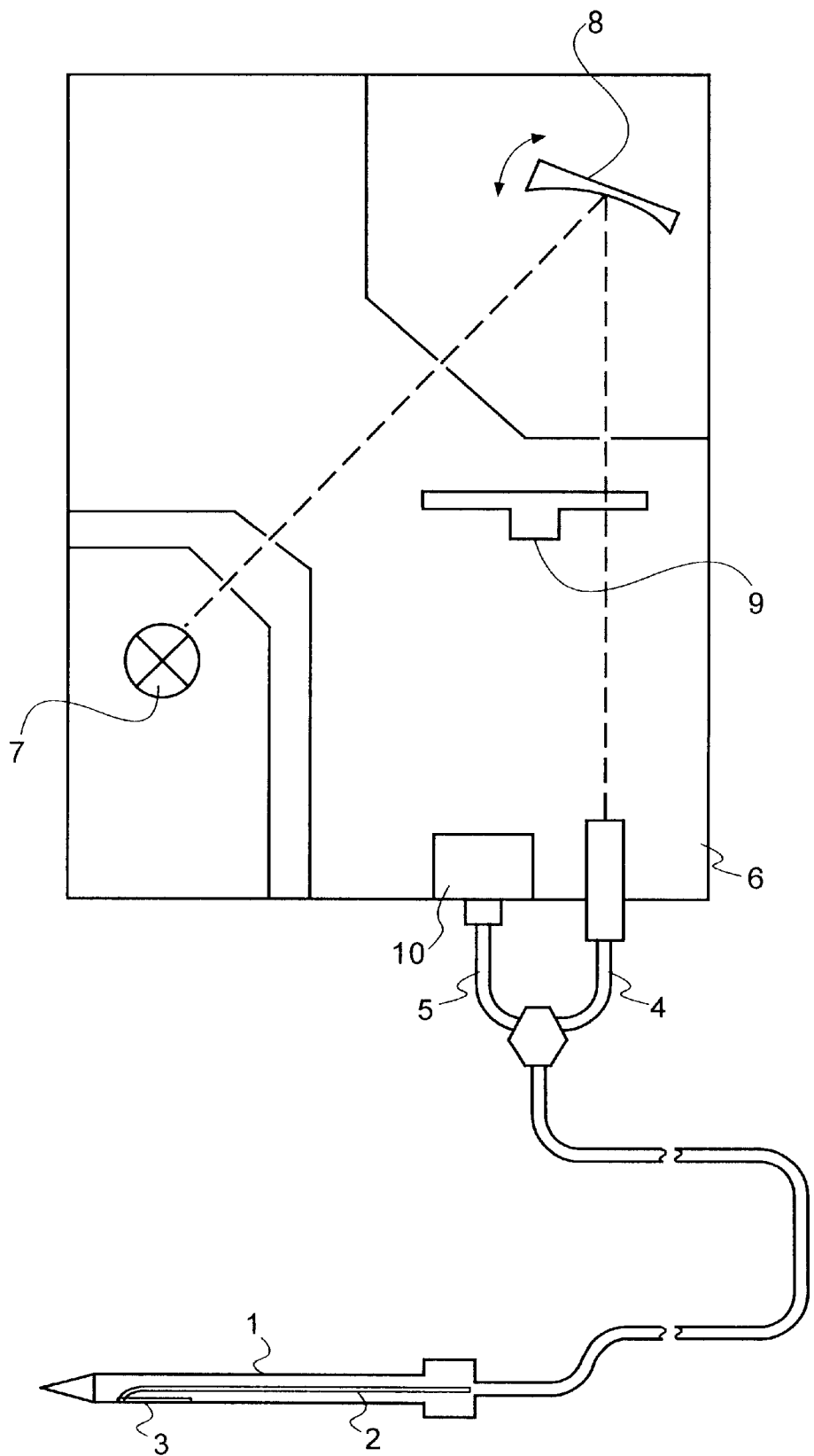

United States Patent
Andersen et al.

[19]

[11] Patent Number: 6,118,542
[45] Date of Patent: Sep. 12, 2000

[54] METHOD AND APPARATUS FOR DETERMINATION OF A QUALITY PROPERTY OF A PIECE OF MEAT

[75] Inventors: Jan Rud Andersen, Kirke Saaby, Denmark; John C. Forrest, West Layfayette, Ind.; Claus Borggaard, Viby Sjaelland; Allan J. Rasmussen, Fuglebjerg, both of Denmark

[73] Assignee: Purdue Research Foundation, West Lafayette, Ind.

[21] Appl. No.: 09/319,910

[22] PCT Filed: Oct. 15, 1998

[86] PCT No.: PCT/DK98/00449

§ 371 Date: Jul. 8, 1999

§ 102(e) Date: Jul. 8, 1999

[87] PCT Pub. No.: WO99/19727

PCT Pub. Date: Apr. 22, 1999

[30] Foreign Application Priority Data

Oct. 15, 1997 [DK]  Denmark ................................ 1179/97

[51] Int. Cl.[7] .................................................... G01N 21/55
[52] U.S. Cl. .................... 356/445; 356/328; 250/339.11; 250/341.8
[58] Field of Search ..................... 356/445, 326, 356/328; 250/339.11, 341.8

[56] References Cited

U.S. PATENT DOCUMENTS 5,239,180   8/1993   Clarke ................................ 250/339.11

FOREIGN PATENT DOCUMENTS 163 453   12/1990   Denmark .
0 444 675   9/1991   European Pat. Off. .

*Primary Examiner*—Robert H. Kim
*Assistant Examiner*—Amanda Merlino
*Attorney, Agent, or Firm*—Tilton, Fallon, Lungmus & Chestnut

[57] ABSTRACT

The invention relates to a method for determination of a quality property of a piece of meat. A light reflection measurement probe is inserted into a muscle of the piece of meat, while the muscle is undergoing the conversion process from living tissue in a newly slaughtered animal to cooled edible meat. The light reflectivity of the muscle is measured by means of a probe in several, different wavelengths or wavelength bands. The probe remains in the muscle for a period of time after this measurement series, while the conversion process in the muscle is proceeding. The light reflectivity of the muscle is measured again in the same wavelengths. The measurement data, possibly after processing, are inserted in an algorithm which expresses the quality property on the basis of changes between the data of the measurement series, and the quality property is automatically calculated in a calculation unit. The probe is removed from the muscle. By means of the present method it has proved possible to predict drip loss in loin muscles within 45 minutes after bleeding of the carcass.

10 Claims, 3 Drawing Sheets

METHOD AND APPARATUS FOR DETERMINATION OF A QUALITY PROPERTY OF A PIECE OF MEAT

The present invention relates to a method and an apparatus for the determination of a quality property of a piece of meat.

Efforts to reduce the fat percentage and increase the muscular mass in pigs may on occasion alter the other meat properties to varying degrees and extents. In particular, the appearance of the fresh cuts is highly important for meat processing companies and may also be of significant importance in the consumers' choice of retail cuts. A deviation in colour of the muscles in a meat cut is seen as less positive. The same is true of colour differences between different cuts or between the muscles in a cut.

The ability of the muscles to hold neat juice is also of significant importance for an impression of quality. If much of the meat juice has migrated to the surface of the cut, the meat looks and feels soft and mushy. The cut may even have a slimy appearance, similar to that produced by bacteria. Poorer ability to hold meat juice also means that the carcass is subject to high drip loss during and after chilling, and that the meat suffers further weight loss during commercial processing. For the consumer, the reduction in quality is marked by visible water on the surface of packed meat or large amounts of blood-like fluid in the base of the pack.

Measuring equipment and methods for determining the juice holding capacity of muscles are known, see especially DK 163.382 C (Slagteriernes Forskningsinstitut). An optical probe is inserted into the muscle and the reflection of the meat adjacent a window in the probe side is measured. Juice holding capacity is determined from a series of measurements carried out while the probe is moved within the muscle. The method requires measurement to be carried out on carcasses which has been chilled for a lengthy period, e.g. 24 hours in chilling room, so that the meat has undergone the biochemical processes associated with the conversion of the living tissue to edible meat. The method cannot be used to determine juice holding capacity on carcasses warm from slaughter.

If the occurrence of muscles of pig meat with reduced quality is to be controlled more effectively than at present, it is important, however, that carcasses with reduced juice holding capacity are detected shortly after slaughter, in order for the information to be passed on immediately so that production can be adjusted accordingly.

It is the objective of the invention to provide a measuring method for detecting the juice holding capacity of meat a short time after slaughter, before the slaughter carcasses are sent to the chilling room.

This objective is achieved in the method according to the invention, which is characterised in that a. a light reflection measuring probe is inserted into a muscle in the piece of meat while the muscle is undergoing the conversion process from living tissue in a newly slaughtered animal to cooled edible meat,
b. the light reflectivity of the muscle is measured by means of the probe in several, different wavelengths or wavelength bands,
c. the probe remains in the muscle for a period of time after this measurement series, while the conversion process in the muscle is proceeding,
d. the light reflectivity of the muscle is measured again in the same wavelengths,
e. steps c and d are if necessary repeated at least one more time,
f. the measurement data, possibly after processing, are inserted in an algorithm which expresses the quality property on the basis of changes between the data of the measurement series,
g. the quality property is automatically calculated in a calculation unit and
h. the probe is removed from the muscle.

By means of the present method, it has proved possible to predict drip loss in loin muscles within 45 minutes after bleeding of the carcass.

The measurements are preferably carried out on-line on a slaughter line on a carcass before it is sent to a chilling room, preferably 0.5 to 2 hours after slaughter.

The series of light reflection measurements are preferably carried out at intervals of between 10 and 300 seconds.

The period of time between the first and last series of reflection measurements is preferably between 1 and 20 minutes.

Measurements are preferably carried out in the near-infrared range from 900 to 1800 nm.

Measurements are preferably carried out in at least two wave lengths or wavelength bands, especially in 4–20 wavelengths or wavelength bands.

An algorithm is preferably used which expresses the juice holding capacity of the piece of meat.

The term piece of meat shall in the present description refer preferably to a slaughter carcass, e.g. a pig or beef carcass.

The apparatus according to the invention for determination of a quality property of a piece of meat is characterised in that it comprises:

a light reflection measuring probe designed for insertion in a muscle of the piece of meat,
a spectrometer arranged to measure the light reflectivity of the muscle in several, different wavelengths or wavelength bands by means of the probe, and
a recording and calculation unit connected to the spectrometer, arranged to store the measurement data obtained, trigger a repetition of the measurement of the muscle's light reflectivity in the same wavelengths a period of time after the first measurement, insert the measurement data obtained in a contained algorithm which expresses the quality property on the basis of changes between the data of the measurement series and automatically calculate the quality property by means of the algorithm and the data of the measurement series.

The apparatus is preferably arranged to repeat a series of light reflection measurements after a period of time of between 10 and 300 seconds.

The apparatus is further preferably arranged to perform the first and last series of reflection measurements within a lapse of time of between 1 and 20 minutes.

Figure 2:
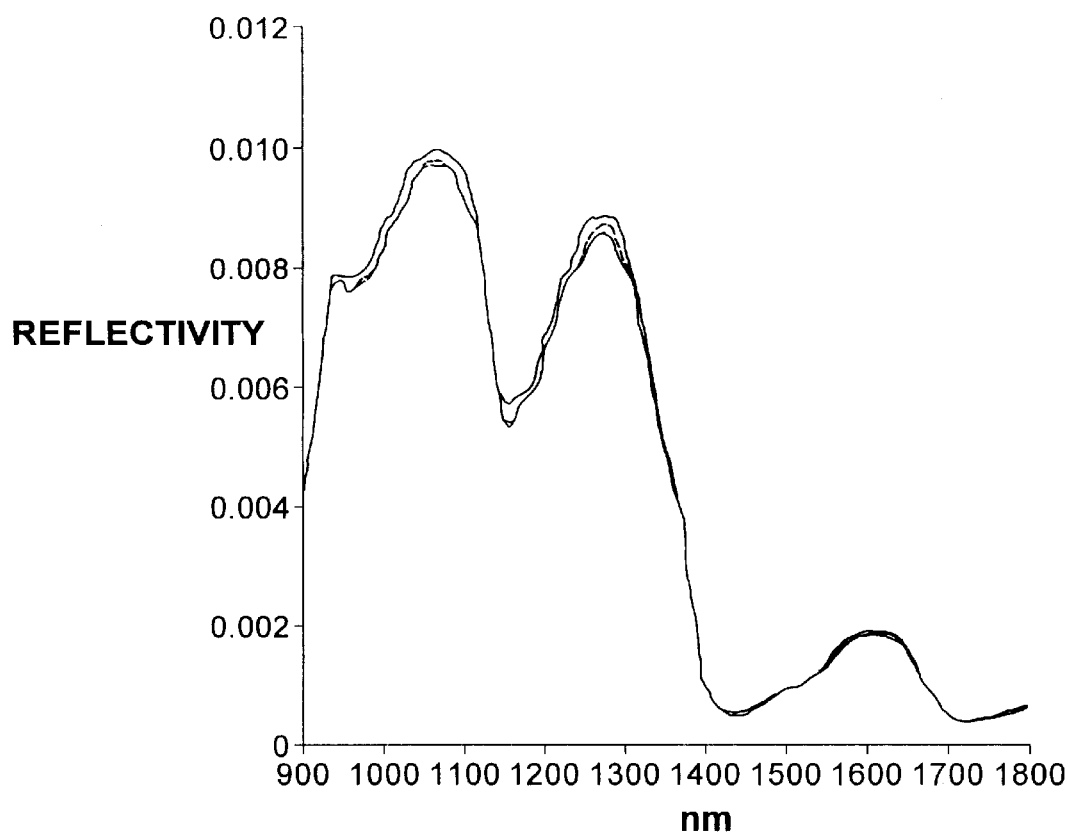
Figure 3:
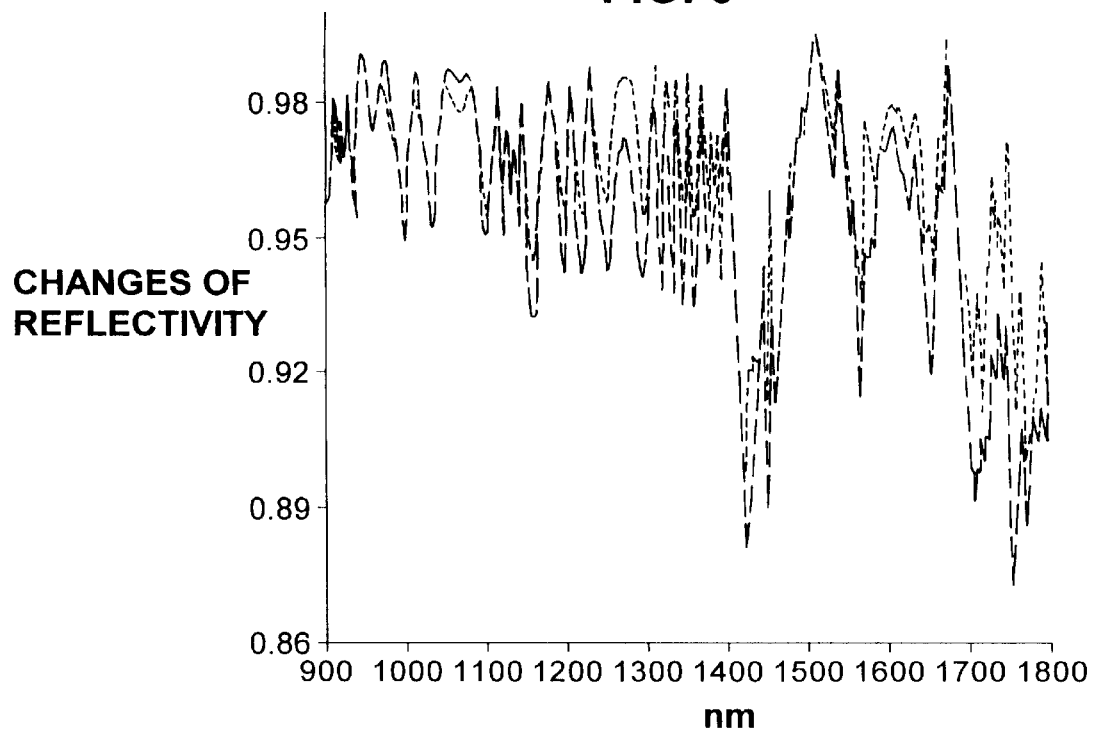
Figure 4:
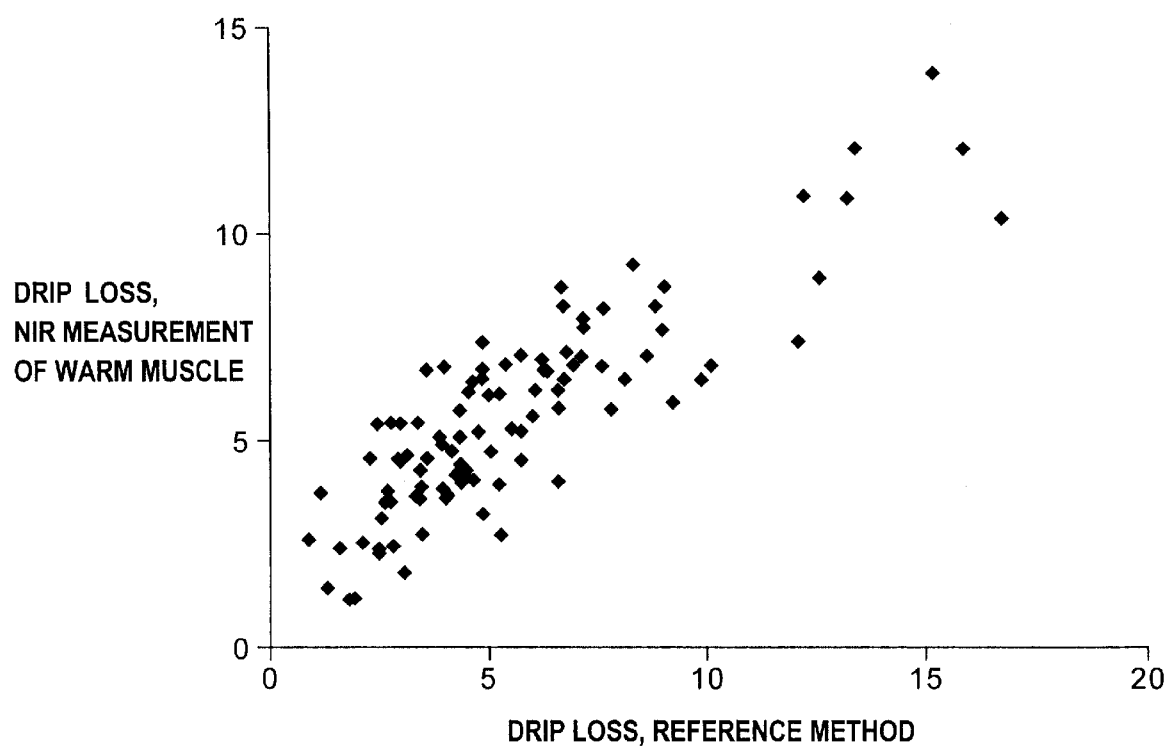

The invention is explained in more detail in the following examples with reference to the drawings, wherein FIG. 1 shows a schematic diagram of an experimental device for recording reflection spectra from muscles warm from slaughter, FIG. 2 shows three reflection spectra recorded at one minute intervals, FIG. 3 shows the second and third reflection spectra after the reflection values have been divided by the reflection values of the first spectrum, and FIG. 4 shows the relationship between values for juice holding capacity determined by a traditional analytical method and by the method according to the invention.

EXAMPLE 1

This example describes an experimental apparatus for measurement of the reflectivity of muscles warm from slaughter in different wavelengths in the near-infrared range by means of an insertion probe.

The apparatus (FIG. 1) comprises a probe 1 designed for insertion into muscles, which probe contains a bundle of quartz fibres 2 (for clarity only one fibre is shown in the probe). In the side of the probe is a window 3 at which the fibre bundle terminates. Outside the probe the fibre bundle is divided at random into two bundles 4 and 5 which lead into a spectrometer 6 of brand Quantum 1200 plus scanning spectrometer from LT Industries, USA. One fibre bundle 4 receives light from a tungsten halogen lamp 7 after the polychromatic light has hit a holographic grating 8 which converts the light to monochromatic light and after it has passed through a rotating perforated disk 9, which changes the light beam to flashes of light. These are conducted through the fibre bundle 4 and shine onto the meat adjacent to the probe window 3. The other fibre bundle 5 captures the light reflected by the meat and transmits it to a detector 10 within the spectrometer. The wavelength of the monochromatic light can be changed by rotating the holographic grating 8. A spectrum from 900 to 1800 nm is traversed.

EXAMPLE 2

This example shows that changes in the reflectivity of muscles warm from slaughter can be measured after a period of time in different wavelengths and that these changes are correlated with the muscles' drip loss (juice holding capacity). The apparatus described in example 1 is used for the experiment.

Measurements are carried out on 16 pig carcasses. They are selected at random at the veterinary inspection of the slaughter line.

40 minutes after bleeding of the pigs, measurements begin, the fibre-optic probe being inserted into the longissimus muscle.

The probe is left in the same position in the carcass loin muscle for a period of five minutes. Over this period, 12 NIR reflection spectra are measured using the spectrometer. The time interval between measurement of spectra is 30 seconds.

FIG. 2 shows the reflection spectra for a loin muscle recorded at 0, 60 and 120 seconds after start of the measuring sequence.

The reflection spectra obtained are processed in the following way:

The first measurement series from the carcass is used as a reference. The reflection values in each of the following 11 spectra are divided by the corresponding reflection values from this reference spectrum. In this way the changes over time in relative reflectivity are obtained for each wavelength (band).

FIG. 3 shows the spectra 60 and 120 seconds after start of the measuring sequence, the reflectivity values being divided by the reflectivity values of the reference spectra. The changes in the spectra can be clearly seen after the processing. The spectra show changes both as a function of time and of frequency.

From each carcass a meat sample is taken for determination of drip loss by a traditional analytical method. 2 g of meat sample are taken adjacent to the eleventh rib 24 hours after slaughter. The sample is hung on a hook in a large centrifuge tube and left for 24 hours at 2° C. The quantity of juice in the base of the tube is weighed. It is seen that the drip loss of the selected carcasses shows only a small variation.

By means of PLS calibration partial least squares) on the data sets obtained, a correlation of more than 0.80 is found between the drip loss determined by a traditional method and drip loss determined by means of NIR probe measurements on carcasses warm from slaughter.

EXAMPLE 3

This experiment is carried out to confirm the results of the experiment of example 2 on a larger scale. Samples are used with a wider drip loss variation. The experiment is carried out over the period of a month at a Danish meat processing plant. For four working days during this period, 102 carcasses are measured.

The experiments are carried out in the same way as example 2 with the probe remaining in the carcass for the whole measuring sequence. The probe is inserted in the longissimus muscle 39 minutes after bleeding and scans are carried out every 30 seconds for the following 6 minutes.

Drip loss in the 102 carcasses is determined as in example 2 by a traditional analytical method. The results achieved vary from approx. 0 to approx. 17 per cent and thus provide a suitable data set for further analysis.

The reflection spectra are treated in the same way as in example 2. PLS calibration gives a correlation between drip loss predicted by the NIR spectra and drip loss determined by the traditional method of over 0.8. The standard deviation of the forecast is approx. 1.8% drip loss. This must be compared with the reproducibility of the reference method, for which the standard deviation is approx. 1%.

FIG. 4 illustrates the results of PLS calibration. The plotted points represent an average of forecasts 60, 90 and 120 seconds after start of data gathering on the carcass.

EXAMPLE 4

This experiment is carried out in similar fashion to the experiments of examples 2 and 3. However, the probe is not left in the carcass, but is removed after each measurement series and reinserted when a new spectrum is to be recorded. The experiment does not give useable results as the variation in spectra due to differences in repositioning of the probe are much higher than the variations taking place in the tissue as a result of rigor processes.

What is claimed is:

1. Method for determination of a quality property of a piece of meat, characterised in that it comprises:
   a. a light reflection measuring probe is inserted into a muscle in the piece of meat while the muscle is undergoing the conversion process from living tissue in a newly slaughtered animal to cooled edible meat,
   b. the light reflectivity of the muscle is measured by means of the probe in several, different wavelengths or wavelength bands,
   c. the probe remains in the muscle for a period of time after this measurement series, while the conversion process in the muscle is proceeding,
   d. the light reflectivity of the muscle is measured again in the same wavelengths,
   e. steps c and d are if necessary repeated at least one more time,
   f. the measurement data, possibly after processing, are inserted in an algorithm which expresses the quality property on the basis of changes between the data of the measurement series,
   g. the quality property is automatically calculated in a calculation unit and
   h. the probe is removed from the muscle.

2. Method according to claim 1, characterised in that the measurements are carried out online on a slaughter line on a carcass before it is sent to a chilling room, preferably 0.5 to 2 hours after slaughter.

3. Method according to claim 1, characterised in that the series of light reflection measurements are carried out at intervals of between 10 and 300 seconds.

4. Method according to claim 1, characterised in that the period of time between the first and last series of reflection measurements is between 1 and 20 minutes.

5. Method according to claim 1, characterised in that measurements are performed in the near-infrared range from 900 to 1800 nm.

6. Method according to claim 1, characterised in that measurements are performed in at least two different wavelengths or wavelength bands, preferably in 4 to 20 wavelengths or wavelength bands.

7. Method according to claim 1, characterised in that an algorithm is used which expresses the juice holding capability of the piece of meat.

8. Apparatus for determination of a quality property of a piece of meat, characterised in that it comprises:

a light reflection measuring probe designed for insertion in a muscle of the piece of meat, a spectrometer arranged to measure the light reflectivity of the muscle in several, different wavelengths or wavelength bands by means of the probe, and a recording and calculation unit connected to the spectrometer, arranged to store the measurement data obtained, trigger a repetition of the measurement of the muscle's light reflectivity in the same wavelengths a period of time after the first measurement, insert the measurement data obtained in a contained algorithm which expresses the quality property on the basis of changes between the data of the measurement series and automatically calculate the quality property by means of the algorithm and the data of the measurement series.

9. Apparatus according to claim 8, characterised in that it is arranged to repeat a series of light reflection measurements after a period of time of between 10 and 300 seconds.

10. Apparatus according to claim 8, characterised in that it is arranged to carry out the first and last series of reflection measurements within a lapse of time of between 1 and 20 minutes.

* * * * *